(12) United States Patent
Zou et al.

(10) Patent No.: US 10,233,135 B2
(45) Date of Patent: Mar. 19, 2019

(54) PROCESS FOR PREPARING PERHYDROFLUORENE OR ALKYL-SUBSTITUTED PERHYDROFLUORENE

(71) Applicant: TIANJIN UNIVERSITY, Tianjin (CN)

(72) Inventors: Jijun Zou, Tianjin (CN); Lun Pan, Tianjin (CN); Xiangwen Zhang, Tianjin (CN); Qingfa Wang, Tianjin (CN); Li Wang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 15/536,569

(22) PCT Filed: Jul. 11, 2016

(86) PCT No.: PCT/CN2016/089625
§ 371 (c)(1),
(2) Date: Jun. 15, 2017

(87) PCT Pub. No.: WO2017/161780
PCT Pub. Date: Sep. 28, 2017

(65) Prior Publication Data
US 2019/0031576 A1    Jan. 31, 2019

(30) Foreign Application Priority Data
Mar. 22, 2016    (CN) .......................... 2016 1 0165310

(51) Int. Cl.
| C07C 1/20 | (2006.01) |
| C07C 2/86 | (2006.01) |
| C07C 29/32 | (2006.01) |
| C07C 45/61 | (2006.01) |
| C07C 13/567 | (2006.01) |

(52) U.S. Cl.
CPC ................ C07C 1/20 (2013.01); C07C 2/864 (2013.01); C07C 2/865 (2013.01); C07C 13/567 (2013.01); C07C 29/32 (2013.01); C07C 45/61 (2013.01); C07C 2603/10 (2017.05)

(58) Field of Classification Search
CPC ........... C07C 1/20; C07C 2/864; C07C 2/865; C07C 13/567; C07C 29/32; C07C 2603/10; C07C 45/61
See application file for complete search history.

(56) References Cited

U.S. PATENT DOCUMENTS

| 3,671,599 A * | 6/1972 | Moore .................... C07C 5/333 585/21 |
| 4,049,733 A * | 9/1977 | Martan ................... C07C 2/865 585/426 |
| 6,037,501 A * | 3/2000 | Saito ........................ C07C 5/32 502/102 |

FOREIGN PATENT DOCUMENTS

CN           105732291          7/2016

OTHER PUBLICATIONS

Bagrii et al., Petroleum Chemistry, 54:2, pp. 100-104 (2014).
Zhang et al., Green Chemistry, 17, p. 4736-4747 (2015).

* cited by examiner

*Primary Examiner* — Youngsul Jeong
*Assistant Examiner* — Jason Y Chong
(74) *Attorney, Agent, or Firm* — Gokalp Bayramoglu

(57) ABSTRACT

The present invention discloses a process for preparing perhydrofluorene or alkyl-substituted perhydrofluorene, comprising the steps of: (1) reacting a phenolic compound or an aromatic hydrocarbon compound or an aromatic ketone compound or an aromatic ether compound with a benzyl compound to carry out an alkylation reaction in the presence of a first catalyst, thereby to produce substituted or unsubstituted diphenyl methane, wherein the first catalyst is an acidic catalyst; and (2) reacting the substituted or unsubstituted diphenyl methane with hydrogen gas to carry out an hydrogenation reaction or a hydrodeoxygenation reaction, thereby to produce perhydrofluorene or alkyl-substituted perhydrofluorene, wherein the second catalyst is a physical mixture of a metal catalyst and an acidic catalyst or a metal catalyst loaded on an acidic catalyst.

6 Claims, No Drawings

PROCESS FOR PREPARING PERHYDROFLUORENE OR ALKYL-SUBSTITUTED PERHYDROFLUORENE

CROSS-REFERENCE TO RELATED APPLICATIONS

This application is a 371 of PCT/CN2016/089625 filed Jul. 11, 2016 which claims benefit of CN 201610165310.8 filed on Mar. 22, 2016, both of which are incorporated herein by reference in their entireties.

FIELD OF THE INVENTION

The invention, in the field of synthesis of high energy density fuels, relates to a process for preparing perhydrofluorene or alkyl-substituted perhydrofluorene.

BACKGROUND OF THE INVENTION

High density fuels are synthesized liquid hydrocarbon compounds, and in essence, the fuels, the same as hydrocarbon fuels refined from petroleum (e.g., aviation kerosene Jet A and rocket kerosene RP-1) can be applied in all air-inhaling engines and rocket engines that use kerosene as fuels. As compared with fuels refined from petroleum, the density of high density fuels increases to a great extent while the mass combustion calorific value is substantially equivalent thereto. Hence, this kind of fuels also can be called as high energy density fuels, and the volume calorific value of the fuels significantly increases. Thus, in the case of a specified volume of oil tanks, the fuels can provide more propulsion power, thereby to significantly increase voyage range or loading ability of aircrafts.

All high density liquid hydrocarbon fuels, e.g., RJ-4, RJ-5, JP-10, are synthesized by Diels-alder addition and hydrogenation with dicyclopentadienyl compounds and acetylene as starting materials. These fuels are derived from fossil resources, including petroleum, coal and the like. Biomass raw materials are also can be used for the preparation of high density fuels. Biomass resources can also be used to prepare high density fuel, wherein the most widely existing biomass resources is lignocellulose, and the lignocellulose derived compounds may be selected from the group consisting of phenol, anisole, guaiacol, cyclohexanone, cyclopentanone, acetone, γ-valerolactone and furfural. Now, high density fuels as prepared by these lignocellulose derived compounds primarily include long chain alkanes, while the synthesized polycyclic hydrocarbon compounds are less. In Green Chemistry 2015, 17 (8), 4473-4481, cyclohexanone is used to prepare composite fuels having a density of 0.887 g/ml. In Scientific Reports 5, Article number: 9565 (2015), cyclopentanol is used to prepare fuels having a density of 0.91 g/ml.

Perhydrofluorene is a tricyclic hydrocarbon compound having a density of up to 1.012 g/ml at 20° C., and thus it can be used as an additive to oil products to increase the density of the oil products. The current process for synthesis of perhydrofluorene is accomplished by reducing fluorene, and the fluorene is prepared by alkylation of benzene and methane dichloride or by intramolecular cyclization of halogen or boric acid-containing diphenyl methane derivatives. Patent EP0911309A1 proposes the scheme that a metal is loaded on an oxide support to convert diphenyl methane derivatives into fluorene-based compounds; the document, Angew. Chem. Int. Ed. 2012, 51, 5359-5362, uses an organic noble metal catalyst to catalyze the dehydrogenation cyclization of diphenyl methane derivatives to produce fluorene; the documents, Angew. Chem. Int. Ed. 2012, 51, 5359-5362; Org. Lett., Vol. 11, No. 20, 2009; J. AM. CHEM. SOC. 9 VOL. 130, NO. 48, 2008, 16159; and Adv. Synth. Catal. 2010, 352, 3267-3274, use a palladium-based catalyst to catalyze the intramolecular cyclization of halogen-containing aromatic hydrocarbons to prepare fluorene-based compounds. The hydrogenation of fluorene into perhydrofluorene is a relatively difficult process. Patent CN102701897A discloses that in a method for preparing cyclic hydrocarbon compounds by hydrogenation of washing oil fraction, at most 32.8% by weight of fluorene can be produced, and the selectivity of the perhydrofluorene only can reach 28.8%. The document, Chem. Eur. J. 2009, 15, 6953-6963, discloses that the yield of the hydrogenation of fluorene into perhydrofluorene only can reach 80% under the conditions of isopropanol as the solvent, RH/C as the catalyst, and hydrogen gas pressure of 5 MPa.

The current process for preparing perhydrofluorene or alkyl-substituted perhydrofluorene is to hydrogenate fluorene or alkyl-substituted fluorene. Fluorene may be derived from the following two sources: first, the fluorene may be prepared from coal tar; high temperature coal tar contains about 1.0 to 2.0% of fluorene, and after cooling, crystallization, and centrifugal separation, it can produce crude fluorene; thereafter, industrial fluorene is dissolved in benzene; after being neutralized and washed with water and solvent removal, the resultant fluorene is re-distilled, and the resultant distillate is recrystallized from gasoline and ethanol to produce fluorene with 95% purity, this method will consume a large quantity of energy; second, the fluorene may be prepared by intramolecular or intermolecular alkylation of halogen or boric acid-containing bicyclic aromatic hydrocarbons, for example, Angewandte Chemie International Edition 2012, 51 (22), 5359-5362 uses the metal Ru to activate the C—H bond of 2,2-diphenylacetic acid to produce fluorene by cyclization; Angewandte Chemie International Edition 2010, 49 (16), 2909-2912 uses Ru to catalyze the crosslinked coupling and intramolecular cyclization of 1,2-dihalobenzene and phenylboric acid to produce fluorene; Advanced Synthesis & Catalysis 2010, 352 (18), 3267-3274 uses palladium to catalyze the intramolecular alkylation of 2-halo-2'-methyl-1,1'-biphenyl to produce fluorene; however, this method has a high cost, and thus it is difficulty industrialized. A process for large-scale production of fluorene is provided that under the catalytic action of aluminum trichloride, methane dichloride and benzene or biphenyl can carry out an alkylation reaction. However, this process will have the following defects: the introduction of toxic benzene, difficult separation and recovery of introduced halogen, high production cost, heavy environmental pollutions, and meanwhile rigorous conditions for reducing fluorene derivatives and a low yield.

DESCRIPTIONS OF THE INVENTION

The objective of the invention is to provide a new process for preparing perhydrofluorene and alkyl-substituted perhydrofluorene. The process comprises the steps: (1) reacting a phenolic compound or an aromatic hydrocarbon compound or an aromatic ketone compound or an aromatic ether compound with a benzyl compound to carry out an alkylation reaction in the presence of a first catalyst, thereby to produce substituted or unsubstituted diphenyl methane, wherein the first catalyst is an acidic catalyst; and (2) reacting the substituted or unsubstituted diphenyl methane with hydrogen gas in the presence of a second catalyst to carry out a hydrogenation reaction or a hydrodeoxygenation reaction, thereby to produce perhydrofluorene or alkyl-substituted perhydrofluorene, wherein the second catalyst is a physical mixture of a metal catalyst and an acidic catalyst or is a metal catalyst loaded on an acidic catalyst.

Preferably, the first catalyst is one or more selected from the group consisting of $SiO_2$—$Al_2O_3$, HZSM-5, Al-MCM-41, Hβ, MMT-K10, SAPO-34, USY, $H_3O_{40}PW_{12} \cdot xH_2O$, Amberlyst-15, Nafion, $AlCl_3$, $FeCl_3$, $ZnCl_2$, $CuCl_2$, metal-modified HPW, $Nb_5O_3$, $WO_3$ or liquid phosphoric acid, wherein the first catalyst is added in an amount of 0.5-26% by weight of the benzyl compound. Preferably, the metal-modified HPM is $Sn_{0.5}TPA$ or HfTPA.

Preferably, the metal catalyst is one or more selected from the group consisting of Cu, W, Mo, Ni, Pd, Pt, Ru, Ir, Rh, Zn, PtNi, CoNi, CoMo, IrFe, PdPt, or RuCu, and the acidic catalyst is one or more selected from the group consisting of $SiO_2$—$Al_2O_3$, HZSM-5, Al-MCM-41, Hβ, MMT-K10, SAPO-34, USY, $H_3O_{40}PW_{12} \cdot xH_2O$, Amberlyst-15, Nafion, $AlCl_3$, $FeCl_3$, $ZnCl_2$, $CuCl_2$, metal-modified HPW ($Sn_{0.5}TPA$, HfTPA), $Nb_2O_5$, $WO_3$ or liquid phosphoric acid; wherein when the metal catalyst and the acidic catalyst are physically mixed, the mass ratio of the metal catalyst to the acidic catalyst is 0.02% or above; when the metal catalyst is loaded on the acidic catalyst, the mass ratio of the metal catalyst to the acidic catalyst is from 0.02 to 10%.

Preferably, the phenol compound is selected from the group consisting of phenol, guaiacol, 3-methylphenol, 2-methylphenol, 3-methoxyphenol, 4-ethylphenol, catechol, 4-vinylphenol, 3-methoxycatechol, 4-ethyl-2-methoxyphenol, 2-methoxy-4-vinylphenol, 2,6-dimethoxyphenol, 4-methyl-2,6-dimethoxy-phenol or 4-allyl-2,6-dimethoxyphenol; the aromatic hydrocarbon compound is selected from the group consisting of benzene, toluene, ethylbenzene, xylene, trimethylbenzene, 2-allylbenzene, 1-ethyl-2-methylbenzene, 1,2,4,5-tetramethylbenzene, naphthalene, and 1-methylnaphthalene; the aromatic ketone compound is selected from the group consisting of benzophenone, acetophenone, propiophenone or 3,4-dimethoxy-1-acetophenone; the aromatic ether compound is selected from the group consisting of anisole, 1-ethyl-4-methoxylbenzene; and the benzyl compound is selected from the group consisting of benzyl alcohol, 2-methylbenzyl alcohol, 4-methylbenzyl alcohol or dibenzyl ether.

Preferably, the alkylation reaction is carried out under the following conditions: reaction temperature is from 50° C. to 200° C., reaction time is from 0.5 to 24 h, molar ratio of the phenolic compound or the aromatic compound or the aromatic ketone compound or the aromatic ether compound to the benzyl compound is from 2:1 to 30:1.

Preferably, the hydrogenation reaction is carried out under the following conditions: mass proportion of the second catalyst to the substituted or unsubstituted diphenyl methane is from 0.01 to 23%, the hydrogen gas pressure is from 3 to 8 MPa, reaction temperature is from 120° C. to 250° C., and reaction time is from 2 to 40 h.

Preferably, the proportion of the metal catalyst in the second catalyst is increased so as to enhance the selectivity of the perhydrofluorene and/or the alkyl-substituted perhydrofluorene.

The perhydrofluorene or alkyl-substituted perhydrofluorene according to the invention may be used as liquid jet fuels.

Beneficial Effects of the Invention

1. In the invention, an acidic catalyst is firstly used to catalyze the alkylation reaction of phenol compounds or aromatic hydrocarbon compounds or aromatic ketone compounds or aromatic ether compounds to produce substituted or unsubstituted diphenyl methane, and then a metal catalysis is used to catalyze hydrogenation/deoxygenation/intramolecular cyclization, to convert the substituted or unsubstituted diphenyl methane into perhydrofluorene or alkyl-substituted perhydrofluorene to be used as high density fuels. During the process, no halogen and no highly toxic materials are introduced, and the catalyst can be recirculated. Thus, the invention provides a new practical process for the preparation of perhydrofluorene alkyl-substituted perhydrofluorene. Surprisingly, the inventor find out that by controlling the ratio of the metal catalyst to the acidic catalyst, the amount of perhydrofluorene and alkyl-substituted perhydrofluorene in fuels can be controlled.

2. The existing technique for synthesis of perhydrofluorene and alkyl-substituted perhydrofluorene can be divided into two stages. First, fluorene derivatives are obtained, and then the derivatives are reduced to provide perhydrofluorene and alkyl-substituted perhydrofluorene. In the process of preparation of the fluorene derivatives, either halogen is introduced or halogen-containing or boric acid-containing diphenyl methane derivatives should be prepared as the raw material. The operation procedure for the process is complex, and will produce heavy pollutions. Furthermore, in the second stage, the conditions for reducing the fluorene derivatives are rigorous, and the corresponding yield is low. Directed to the problems as involved in the first stage, the invention uses phenol or aromatic hydrocarbon or aromatic ketone or aromatic ether compounds derived from lignocellulose as the raw material, and by a simple alkylation reaction, the invention produces substituted or unsubstituted diphenyl methane which has similar function to halogen by substituting halogen with natural oxygen-containing functional groups. The process has the advantages of a green source of raw materials, being easily industrialized, low cost and environmental friendliness. Directed to the problems regarding to the intramolecular cyclization and difficult hydrogenation of fluorene and derivatives thereof, the process according to the invention can effectively combine the intramolecular cyclization and the hydrogenation/deoxygenation, so as to achieve the one-stage production of perhydrofluorene or alkyl-substituted perhydrofluorene. The conditions for the process are mild, and the selectivity of the product is controllable. The process is a first finding by the inventor.

3. Directed to the problem that biomass fuels obtained by mass production have low density, in order to obtain high density (or high energy density) hydrocarbon compounds, it is necessary to increase the number of rings in the hydrocarbon compounds. The invention, starting from lignocellulose, prepares biomass fuels containing tricyclic perhydrofluorene and alkyl-substituted perhydrofluorene, thereby to greatly increase the density of the biomass fuels, and thus provides fuels having high energy density. Furthermore, the invention increases the selectivity of perhydrofluorene and/or alkyl-substituted perhydrofluorene.

4. The inventor surprisingly finds out that under the condition that the lignocellulose and the amount of corresponding catalyst are defined, by continuously adding benzyl compounds while keeping the molar ratio of the lignocellulose derivatives to the benzyl compounds to be 30:1, the lignocellulose derivatives may be completely converted, and the selectivity is very high.

EXAMPLES

The following examples are described to further illustrate the embodiments of the invention. The examples are only illustrative but not restrictive.

In the invention, lignocellulose derivatives (i.e., some phenolic compound or an aromatic hydrocarbon compound or an aromatic ketone compound or an aromatic ether compound, wherein the phenolic compounds are selected from the group consisting of phenol, guaiacol, 3-methylphenol, 2-methylphenol, 3-methoxyphenol, 4-ethylphenol, catechol, 4-vinylphenol, 3-methoxycatechol, 4-ethyl-2-methoxyphenol, 2-methoxy-4-vinylphenol, 2,6-dimethoxyphenol, 4-methyl-2,6-dimethoxy-phenol or 4-allyl-2,6-dimethoxyphenol; the aromatic hydrocarbon compounds are selected from the group consisting of benzene, toluene, ethylbenzene, xylene, trimethylbenzene, 2-allylbenzene, 1-ethyl-2-methylbenzene, 1,2,4,5-tetramethylbenzene, naphthalene, and 1-methylnaphthalene; the aromatic ketone compounds are selected from the group consisting of benzophenone, acetophenone, propiophenone or 3,4-dimethoxy-1-acetophenone; and the aromatic ether compounds are selected from the group consisting of anisole, 1-ethyl-4-methoxylbenzene) and the benzyl compound (selected from the group consisting of 2-methylbenzyl alcohol, 4-methylbenzyl alcohol, isomers of 2-methylbenzyl alcohol, benzyl alcohol and dehydration-condensing product of benzyl alcohol, i.e., dibenzyl ether) are carried out the alkylation reaction to produce diphenyl methane derivatives (substituted or unsubstituted diphenyl methane), and then by dehydrogenation/deoxygenation/intramolecular cyclization, a mixture in which perhydrofluorene or alkyl-substituted perhydrofluorene are main component or pure perhydrofluorene or alkyl-substituted perhydrofluorene can be produced.

The process is accomplished in two steps. The first step is the alkylation reaction, and in this step, the lignocellulose derivatives and the benzyl compound are carried out the alkylation reaction in the presence of an acidic catalyst (selected from the group consisting of $SiO_2$—$Al_2O_3$, HZSM-5, Al-MCM-41, Hβ, MMT-K10, SAPO-34, USY, $H_3O_{40}PW_{12} \cdot xH_2O$ (HPW), Amberlyst-15, Nafion, $AlCl_3$, $FeCl_3$, $ZnCl_2$, $CuCl_2$, metal-modified HPW (e.g., $Sn_{0.5}$TPA, HfTPA), metal oxides including $Nb_2O_5$, $WO_3$ and liquid phosphoric acid) while keeping the molar ratio of the two reactants to be 2:1 to 30:1 at the reaction temperature of from 50 to 200° C., to produce diphenyl methane derivatives (substituted or unsubstituted diphenyl methane). The lignocellulose derivatives, being compounds having oxygen-containing functional group, are either some phenolic compounds or aromatic ketone compounds or aromatic ether compounds obtained by thermal cleavage or acid catalytic hydrolysis of lignocellulose, or some aromatic hydrocarbons obtained by deoxygenation of these phenolic compounds, or some alkyl aromatic hydrocarbon compounds obtained by transalkylation, including toluene, xylene, trimethylbenzene, ethylbenzene, 1-ethyl-2-methylbenzene, 2-allyl-benzee, 1,2,4,5-tetramethylbenzene, naphthalene, 1-methylnaphthalene, etc.; the benzyl compounds include 2-methylbenzylalcohol, 4-methylbenzyl alcohol, isomers of 2-methylbenzyl alcohol, benzyl alcohol and dehydration condensing product of benzyl alcohol, i.e., dibenzyl ether. The catalyst is added in an amount of 0.5 to 26% by weight of the benzyl compound, and the reaction time is from 0.5 to 24 h. After the reaction, diphenyl methane derivatives are separated by vacuum distillation.

In the second step, deoxygenation/cyclisation/hydrogenation of diphenyl methane derivatives (substituted or unsubstituted diphenyl methane) are carried out. An amount of diphenyl methane derivatives are reacted in the presence of a physical mixture of a metal catalyst (Cu, W, Mo, Ni, Pd, Pt, Ru, Ir, Rh, and Zn) or a bimetal catalyst (PtNi, CoNi, CoMo, IrFe, PdPt, and RuCu, etc.) and an acid catalyst ($SiO_2$—$Al_2O_3$, HZSM-5, Al-MCM-41, Hβ, MMT-K10, SAPO-34, USY, $H_3O_{40}PW_{12} \cdot xH_2O$ (HPW), Amberlyst-15, Nafion, $AlCl_3$, $FeCl_3$, $ZnCl_2$, $CuCl_2$, metal-modified HPW (e.g., $Sn_{0.5}$TPA, HfTPA), metal oxides including $Nb_2O_5$ and $WO_3$ and liquid phosphoric acid) or a metal catalyst loaded on an acid catalyst (to keep the mass proportion of the metal catalyst to the acid support to be above 0.02%, the loading amount of the loading catalyst is in the range of 0.02 to 10%) under the hydrogen pressure of 3 to 8 MPa and at the temperature from 120 to 250° C. for 2 to 40 h, to produce a mixture in which the proportion of perhydrofluorene and alkyl-substituted perhydrofluorene is controllable or pure perhydrofluorene and alkyl-substituted perhydrofluorene.

Example 1

25.2 g of anisole, 2.08 g of dibenzyl ether, and 0.1 g of MMT-K10 were charged into a 50 ml three-necked flask, and with magnetic stirring, the mixture was reacted at 110° C. for 2 hours. The above reaction mixture was transferred into a distillation apparatus to be purified by vacuum distillation, and the fractions at the temperature of 160 to 210° C. are collected under the pressure of −0.08 MPa, to produce 6 g of colorless organic fraction.

Gas chromatography is used to analyze the alkylation product (diphenyl methane derivatives), and the resultant results are shown as follows: the conversion rate of dibenzyl ether is 100%, the conversion rate of anisole is 15%, and the yield of diphenyl methane derivatives (i.e., substituted or unsubstituted diphenyl methane) is 90%. After vacuum distillation, pure diphenyl methane or a substituted diphenyl methane mixture can be produced.

Examples 2-18

As Example 1, $SiO_2$—$Al_2O_3$, HZSM-5, Al-MCM-41, Hβ, MMT-K10, SAPO-34, USY, $H_3O_{40}PW_{12} \cdot xH_2O$ (HPW), Amberlyst-15, Nafion, $AlCl_3$, $FeCl_3$, $ZnCl_2$, $CuCl_2$, metal-modified HPW (e.g., $Sn_{0.5}$TPA, HfTPA), metal oxides including $Nb_2O_5$, $WO_3$ and liquid phosphoric acid each can be used to catalyze the alkylation reaction between benzene ring-containing derivatives of lignocellulose and the benzyl compound (selected from the group consisting of 2-methylbenzyl alcohol, 4-methylbenzyl alcohol, isomers of 2-methylbenzyl alcohol, benzyl alcohol, and dehydration condensing product of benzyl alcohol, i.e., dibenzyl ether). Now, the results regarding to the catalyst and amount thereof, conversion rate of reactants, reactant ratios, reaction temperature, reaction time, and yield of diphenyl methane derivatives (i.e., substituted or unsubstituted diphenyl methane) are listed in Table 1:

TABLE 1

| Examples | Raw material 1 and mass thereof | Raw material 2 and mass thereof | Raw material 1/raw material 2 | Catalyst | Mass of catalysts (g) | Reaction temperature (° C.) | Reaction time (h) | Conversion rate of raw material 1 (%) | Conversion rate of raw material 2 (%) | Selectivity of diphenyl methane derivatives (%) |
|---|---|---|---|---|---|---|---|---|---|---|
| 2 | Phenol 21.93 g | Dibenzyl ether 46.20 g | 1:1 | $Sn_{0.5}$TPA | 6.8 | 110 | 6 | 100 | 100 | 65 |

TABLE 1-continued

| Examples | Raw material 1 and mass thereof | Raw material 2 and mass thereof | Raw material 1/raw material 2 | Catalyst | Mass of catalysts (g) | Reaction temperature (° C.) | Reaction time (h) | Conversion rate of raw material 1 (%) | Conversion rate of raw material 2 (%) | Selectivity of diphenyl methane derivatives (%) |
|---|---|---|---|---|---|---|---|---|---|---|
| 3 | Anisole 25.20 g | 2-Methylbenzyl alcohol 1.90 g | 15:1 | HZSM-5 | 0.2 | 110 | 4 | 6 | 100 | 93 |
| 4 | Trimethyl benzene 28.01 g | Dibenzyl ether 1.54 g | 30:1 | SAPO-34 | 0.1 | 110 | 1.5 | 7.0 | 100 | 100 |
| 5 | Xylene 24.74 g | Benzyl alcohol 12.59 g | 2:1 | USY | 6.8 | 50 | 18 | 28 | 100 | 72 |
| 6 | Ethylbenzene 24.74 g | Dibenzyl ether 2.31 g | 20:1 | $H_3O_{40}PW_{12} \cdot xH_2O$ (HPW) | 0.1 | 160 | 0.5 | 10.8 | 100 | 95 |
| 7 | 1-Ethyl-2-methylbenzene 28.01 g | Benzyl alcohol 8.40 g | 10:1 | $AlCl_3$ | 6.8 | 160 | 13 | 8.3 | 100 | 85 |
| 8 | Benzene 18.20 g | Dibenzyl ether 7.70 g | 5:1 | $FeCl_3$ | 7.0 | 110 | 8 | 30 | 100 | 80 |
| 9 | 2-Allyl benzene 27.54 g | Dibenzyl ether 15.4 g | 3:1 | HfTPA | 0.3 | 130 | 1.8 | 55 | 100 | 78 |
| 10 | Acetophenone 28.00 g | Dibenzyl ether 7.70 g | 6:1 | Al-MCM-41 | 0.3 | 130 | 1.8 | 38.1 | 100 | 82 |
| 11 | 1,2,4,5-Tetramethylbenzene 31.28 g | Dibenzyl ether 3.85 g | 12:1 | Amberlyst-15 | 7.0 | 50 | 20 | 16.6 | 100 | 88 |
| 12 | Guaiacol 28.93 g | 4-Methylbenzyl alcohol 28.47 g | 1:1 | $ZnCl_2$ | 7.2 | 110 | 12 | 58 | 100 | 67 |
| 13 | 1-Ethyl-4-methoxybenzene 31.74 g | Dibenzyl ether 3.08 g | 15:1 | $CuCl_2$ | 0.3 | 110 | 2 | 12.4 | 100 | 90 |
| 14 | 2-Methylphenol 25.20 g | Dibenzyl ether 2.57 g | 18:1 | $Nb_2O_5$ | 7.2 | 200 | 6 | 10 | 100 | 95 |
| 15 | 3-Methoxyphenol 28.93 g | Dibenzyl ether 3.08 g | 15:1 | $SiO_2-Al_2O_3$ | 0.3 | 110 | 3.5 | 12 | 100 | 92.3 |
| 16 | 4-Ethylphenol 28.47 g | Dibenzyl ether 1.54 g | 30:1 | $WO_3$ | 0.1 | 200 | 0.5 | 6.8 | 100 | 100 |
| 17 | 3-Methoxy catechol 32.66 g | Benzyl alcohol 25.20 g | 1:1 | Nafion | 7.2 | 50 | 24 | 58 | 100 | 68 |
| 18 | 2,6-dimethoxyphenol 35.92 g | Dibenzyl ether 1.85 g | 25:1 | phosphoric acid | 7.2 | 50 | 24 | 7.5 | 100 | 97 |

As seen from the above examples 1-18, the lignocelluloses derivatives (phenolic or aromatic hydrocarbon or aromatic ketone or aromatic ether compounds) and a benzyl compound may be reacted in a molar ratio from 2:1 to 30:1 at the temperature of from 50 to 200° C., to reach a conversion rate above 6%. The benzyl compound may be fully converted. The lower the proportion of the benzyl compound, the higher the yield of the bicyclic compound. When the ratio of the lignocellulos derivatives to the benzyl compound is 30:1, the selectivity of the alkylation product can reach 100%. The higher temperature will allow the benzyl compound to more easily carry out the self-transformation, thereby to produce side products. As to all acidic catalysts as listed, the same reaction can occur. All lignocellulose derivatives (including phenolic or aromatic hydrocarbon or aromatic ketone or aromatic ether compounds) can carry out the alkylation reaction with a benzyl compound (including 2-methylbenzyl alcohol, 4-methylbenzyl alcohol, isomers of 2-methylbenzyl alcohol, benzyl alcohol and dehydration condensing product of benzyl alcohol, i.e., diphenyl ether) in the presence of the acidic catalysts as listed here. However, the high the acidity, the shorter the reaction time, and thus the benzyl derivatives are more inclined to involve in side reactions.

Example 19

30 g of o-benzyl anisole, 3.6 g of palladium on carbon, and 3 g of HZSM-5 catalyst were added to a 100 ml autoclave with stirring device, in which the palladium on carbon comprises 5 weight percent of palladium and the stirring speed is 680 rpm. The resultant mixture was hydrogenated under the hydrogen gas pressure of 6 MPa and at 200° C. for 10 hours, and after centrifugal separation, 26 g of colorless organic liquid was produced.

GG-MS analysis was used to analyze the prepared fuel to show that the product is consisted of two components (a mixture including 35% by weight of dicyclohexylmethane and 65% by weight of perhydrofluorene).

Examples 20-34

As Example 19, a physical mixture of a metal catalyst (Cu, W, Mo, Ni, Pd, Pt, Ru, Ir, Rh, Zn, etc.) or a bimetal catalyst (PtNi, CoNi, CoMo, IrFe, PdPt, RuCu, etc.) and an acidic catalyst (SiO$_2$—Al$_2$O$_3$, HZSM-5, Al-MCM-41, Hβ, MMT-K10, SAPO-34, USY, H$_3$O$_{40}$PW$_{12}$.xH$_2$O (HPW), Amberlyst-15, Nafion, AlCl$_3$, FeCl$_3$, ZnCl$_2$, CuCl$_2$, metal-modified HPW (e.g., Sn$_{0.5}$TPA, HfTPA), metal oxides including Nb$_2$O$_5$ and WO$_3$ and liquid phosphoric acid) or a metal catalyst loaded on an acidic catalyst (to keep the mass proportion of the metal catalyst to the acidic catalyst to be above 0.02%, the loading amount of the loading catalyst is in the range of 0.02 to 10%) can catalyze the HDO (hydrogenation, deoxygenation) and cyclization of diphenyl methane derivatives (i.e., substituted or unsubstituted diphenyl methane). Catalysts and amounts thereof, reaction temperature, reaction pressure, reaction time, and variations in the fuel yield are shown in Table 2:

compound in the product. The formation of tricyclic hydrocarbon compounds can lead to further increase in the density of the resultant fuels.

The density of pure perhydrofluorene can reach 1.012 g·ml$^{-1}$ at 20° C., and the density of pure dicyclohexylmethane can reach 0.8750 g·ml$^{-1}$ at 20° C. As to the mixtures of the above two compounds as prepared in the examples, e.g., the mixture in Example 19, the density is 0.9172 g·ml$^{-1}$ as determined according to GB2540-81 "Petroleum Products—Determination of Density-Pyknometer Method", and the ice point is lower than −60° C. as determined according to GB2430-81 "Determination of the Ice Point of Jet Fuel"; and the dynamic viscosity is 10.41 mm$^2$/s as determined according to GB265-88 "Petroleum Products—Determina-

TABLE 2

| Examples | reactants and amounts thereof | Catalysts and amounts thereof | Reaction time (h) | Reaction temperature (° C.) | hydrogen gas pressure (MPa) | Product yield (%) | |
|---|---|---|---|---|---|---|---|
| | | | | | | dicyclohexyl methane | perhydrofluorene |
| 20 | o-benzyl phenol 30 g | Pd/C 5 g | 10 | 200 | 6 | 0 | 100 |
| 21 | 1,2-dihydroxyl-4-benzylbezene 30 g | Rainey nickel 7 g + WO3 3 g | 22 | 250 | 5 | 30 | 70 |
| 22 | 4-benzyl-2,6-dimethoxyphenol 30 g | Ru 3 g + FeCl$_3$ 3 g | 6 | 150 | 4 | 61 | 39 |
| 23 | 2-benzyl-5-dimethoxybenzene 30 g | Rh 2 g + AlCl$_3$ 3 g | 9 | 120 | 3 | 65 | 35 |
| 24 | 1-methyl-2-(4-methylbenzene) benzene 30 g | Pt 4 g + phosphoric acid 1.5 g | 8 | 180 | 5 | 40 | 60 |
| 25 | 1-benzyl-2-dimethylbenzene 30 g | PdPt 5 g + HZSM-5 3 g | 2 | 250 | 5 | 35 | 65 |
| 26 | Diphenyl methane 30 g | Ir 0.5 g + Sn$_{0.5}$TPA 3 g | 15 | 220 | 4 | 78 | 22 |
| 27 | o-benzyl anisole 30 g | PtNi 3.6 g | 8 | 200 | 4 | 0 | 100 |
| 28 | 1-Ethyl, 2-benzyl, 4-methoxybenzene 30 g | IrFe 1.8 g + HfTPA 3 g | 9 | 150 | 5 | 58 | 42 |
| 29 | o-benzyl, 4-methoxyphenol 30 g | RuCu 8 g + Hβ 3 g | 20 | 250 | 4 | 9 | 91 |
| 30 | 1-Ethyl, 4-methoxy-2-(2-methylbenzene) benzene 30 g | CoMo 8 g + USY 3 g | 25 | 210 | 6 | 16 | 84 |
| 31 | 1-ethyl-2-(2-methylbenzene) benzene 30 g | CoNi 1.8 g + SAPO-34 3 g | 26 | 190 | 8 | 63 | 37 |
| 32 | 4-benzyl-1-ethyl-2-methylbenzene 30 g | Mo 1.8 g + Nb$_2$O$_5$ 3 g | 30 | 200 | 8 | 72 | 28 |
| 33 | 1,2-dihydroxy-3-benzyl-6-methoxybenzene 30 g | W 1.8 g + CuCl$_2$ 3 g | 35 | 250 | 7 | 89 | 11 |
| 34 | 2-benzyl-4-ethylphenol 30 g | Zn 1.8 g + ZnCl$_2$ 3 g | 40 | 250 | 7 | 92 | 8 |

As seen from Examples 19-34, the combination of a metal site and an acidic site can catalyze the diphenyl methane derivatives (i.e., substituted or unsubstituted diphenyl methane) to carry out the HDO reaction, and under the hydrogen pressure of 3 to 8 MPa and at the temperature from 120 to 250° C., the conversion rate can reach 100%, to produce a mixture of the saturated dicyclohexylmethane hydrocarbon derivative, and perhydrofluorene and alkyl-substituted perhydrofluorene. The formation of perhydrofluorene and alkyl-substituted perhydrofluorene is special phenomena. A single metal site can catalyze diphenyl methane derivatives to produce pure perhydrofluorene which is a saturated hydrocarbon derivative. In normal situations, the diphenyl methane derivatives can produce the saturated dicyclohexylmethane hydrocarbon derivative. The intramolecular cyclization is combined with the HDO process to produce a tricyclic compound, and the higher the proportion of the metal catalyst, the higher the proportion of the tricyclic compound in the product. The formation of tricyclic hydrocarbon compounds can lead to further increase in the density of the resultant fuels.

tion Kinematic Viscosity and Dynamic Viscosity". As seen from these results, the mixture obtained after hydrogenation and deoxygenation of dicyclohexylmethane is a good fuel or a fuel additive.

The invention claimed is:

1. A process for preparing perhydrofluorene or alkyl-substituted perhydrofluorene, characterized in that the process comprises steps of:
   (1) reacting a phenolic compound or an aromatic hydrocarbon compound or an aromatic ketone compound or an aromatic ether compound with a benzyl compound to carry out an alkylation reaction in the presence of a first catalyst, thereby to produce substituted or unsubstituted diphenyl methane, wherein the first catalyst is an acidic catalyst; and
   (2) reacting the substituted or unsubstituted diphenyl methane with hydrogen gas in the presence of a second catalyst to carry out a hydrogenation reaction or a hydrodeoxygenation reaction, thereby to produce perhydrofluorene or alkyl-substituted perhydrofluorene, wherein the second catalyst is a physical mixture of a metal catalyst and an acidic catalyst or is a metal catalyst loaded on an acidic catalyst;

wherein the metal catalyst is one or more selected from the group consisting of Cu, W, Mo, Ni, Pd, Pt, Ru, Ir, Rh, Zn, PtNi, CoNi, CoMo, IrFe, PdPt, or RuCu, and the acidic catalyst is one or more selected from the group consisting of $SiO_2$—$Al_2O_3$, HZSM-5, Al-MCM-41, Hβ, MMT-K10, SAPO-34, USY, $H_3O_{40}PW_{12} \cdot xH_2O$, Amberlyst-15, Nafion, $AlCl_3$, $FeCl_3$, $ZnCl_2$, $CuCl_2$, metal-modified HPW, $Nb_2O_5$, $WO_3$ or liquid phosphoric acid;

wherein when the metal catalyst and the acidic catalyst are physically mixed, a mass ratio of the metal catalyst to the acidic catalyst is 0.02% or above; and when the metal catalyst is loaded on the acidic catalyst, the mass ratio of the metal catalyst to the acidic catalyst is from 0.02 to 10%.

2. The process for preparing perhydrofluorene or alkyl-substituted perhydrofluorene according to claim 1, characterized in that the first catalyst is one or more selected from the group consisting of $SiO_2$—$Al_2O_3$, HZSM-5, Al-MCM-41, Hβ, MMT-K10, SAPO-34, USY, $H_3O_{40}PW_{12} \cdot xH_2O$, Amberlyst-15, Nafion, $AlCl_3$, $FeCl_3$, $ZnCl_2$, $CuCl_2$, metal-modified HPW, $Nb_2O_5$, $WO_3$ or liquid phosphoric acid, wherein the first catalyst is added in an amount of 0.5-26% by weight of the benzyl compound.

3. The process for preparing perhydrofluorene or alkyl-substituted perhydrofluorene according to claim 2, characterized in that the metal modified HPW is $Sn_{0.5}TPA$ or HfTPA.

4. The process for preparing perhydrofluorene or alkyl-substituted perhydrofluorene according to claim 1, characterized in that the phenolic compound is selected from the group consisting of phenol, guaiacol, 3-methylphenol, 2-methylphenol, 3-methoxyphenol, 4-ethylphenol, catechol, 4-vinylphenol, 3-methoxycatechol, 4-ethyl-2-methoxyphenol, 2-methoxy-4-vinylphenol, 2,6-dimethoxyphenol, 4-methyl-2,6-dimethoxy-phenol or 4-allyl-2,6-dimethoxy-phenol; the aromatic hydrocarbon compound is selected from the group consisting of benzene, toluene, ethylbenzene, xylene, trimethylbenzene, 2-allylbenzene, 1-ethyl-2-methylbenzene, 1,2,4,5-tetramethylbenzene, naphthalene, and 1-methylnaphthalene; the aromatic ketone compound is selected from the group consisting of benzophenone, acetophenone, propiophenone or 3,4-dimethoxy-1-acetophenone; the aromatic ether compound is selected from the group consisting of anisole, 1-ethyl-4-methoxylbenzene; and the benzyl compound is selected from the group consisting of benzyl alcohol, 2-methylbenzyl alcohol, 4-methylbenzyl alcohol or dibenzyl ether.

5. The process for preparing perhydrofluorene or alkyl-substituted perhydrofluorene according to claim 1, characterized in that the alkylation reaction is carried out under the following conditions: reaction temperature is from 50 to 200° C., reaction time is 0.5 to 24 h, and molar ratio of the phenolic compound or the aromatic hydrocarbon compound or the aromatic ketone compound or the aromatic ether compound to the benzyl compound is from 2:1 to 30:1; the hydrogenation reaction is carried out under the following conditions: mass ratio of the second catalyst to the substituted or unsubstituted diphenyl methane is from 0.01% to 23%, hydrogen gas pressure is from 3 to 8 MPa, reaction temperature is from 120° C. to 250° C., and reaction time is from 2 to 40 h.

6. The process for preparing perhydrofluorene or alkyl-substituted perhydrofluorene according to claim 1, characterized in that a proportion of the metal catalyst in the second catalyst is increased so as to enhance a selectivity of the perhydrofluorene and/or the alkyl-substituted perhydrofluorene.

* * * * *